US009145386B2

(12) United States Patent
García-España Monsonís et al.

(10) Patent No.: US 9,145,386 B2
(45) Date of Patent: Sep. 29, 2015

(54) SOD-IMITATING METAL COMPLEXES

(75) Inventors: Enrique García-España Monsonís, Valencia (ES); Mª Paz Clares García, Valencia (ES); Salvador Blasco Llopis, Valencia (ES); Concepción Soto Soriano, Valencia (ES); Jorge González García, Valencia (ES); Begoña Verdejo Viu, Valencia (ES)

(73) Assignee: UNIVERSITAT DE VALENCIA (ES)

( * ) Notice: Subject to any disclaimer, the term of this patent is extended or adjusted under 35 U.S.C. 154(b) by 560 days.

(21) Appl. No.: 13/497,135

(22) PCT Filed: Sep. 20, 2010

(86) PCT No.: PCT/ES2010/070607
§ 371 (c)(1),
(2), (4) Date: Mar. 26, 2012

(87) PCT Pub. No.: WO2011/033163
PCT Pub. Date: Mar. 24, 2011

(65) Prior Publication Data
US 2012/0178730 A1    Jul. 12, 2012

(30) Foreign Application Priority Data
Sep. 21, 2009    (ES) .................... 200930712

(51) Int. Cl.
  *C07D 255/04*    (2006.01)
  *A61K 31/395*    (2006.01)
  *C07D 401/12*    (2006.01)
(52) U.S. Cl.
  CPC .................... *C07D 401/12* (2013.01)

(58) Field of Classification Search
None
See application file for complete search history.

(56) References Cited

U.S. PATENT DOCUMENTS

| 6,794,371 B1 | 9/2004 | Frank |
| 2007/0298354 A1 | 12/2007 | Ding et al. |
| 2008/0085883 A1 | 4/2008 | Piganelli et al. |

FOREIGN PATENT DOCUMENTS

EP    1392328 B1    3/2004

OTHER PUBLICATIONS

Hileman. Expert Opinion on Therapeutic Targets, 2001, 5(6), 697-710.*
Gonzalez. Organic and Biomolecular Chemistry, 2010, 8, 2367-76.*

* cited by examiner

*Primary Examiner* — Noble Jarrell
(74) *Attorney, Agent, or Firm* — Tristan A. Fuierer; Moore & Van Allen, PLLC

(57) ABSTRACT

The present invention comprises a process to synthesise metal complexes from macrocyclic polyazapyridinophane compounds characterised as superoxide dismutase enzyme (SOD) mimetics. Furthermore, the present invention relates to the macrocyclic polyazapyridinophane compounds themselves, the metal complexes formed from these and to their use in the treatment of diseases the aetiology of which is based on disturbances in the activity of, or a deficiency in endogenous SOD, mainly as anti-inflammatories, analgesics and antioxidant compounds providing protection against cellular oxidative stress.

21 Claims, 5 Drawing Sheets

SOD-IMITATING METAL COMPLEXES

CROSS-REFERENCE TO RELATED APPLICATIONS

This application is filed under the provisions of 35 U.S.C. §371 and claims the priority of International Patent Application No. PCT/ES2010/070607 filed on 20 Sep. 2010 entitled "SOD-Imitating Metal Complexes" in the name of Enrique GARCÍA-ESPAÑA MONSONÍS, et al., which claims priority to Spanish Patent Application No. P200930712 filed on 21 Sep. 2009, both of which are hereby incorporated by reference herein in their entirety.

FIELD OF INVENTION

The present invention relates to a process for the synthesis of metal complexes from macrocyclic polyazapyridinophane compounds characterised as superoxide dismutase enzyme (SOD) mimetics. Furthermore, the present invention relates to the macrocyclic polyazapyridinophane compounds themselves, the metal complexes formed from these and their use in the treatment of diseases whose aetiology is rooted in disturbances in the activity of, or a deficiency in endogenous SOD, mainly as anti-inflammatories, analgesics and as anti-oxidants providing protection against cellular oxidative stress.

STATE OF THE ART

The dismutation of superoxide ($O_2^-$) into oxygen and hydrogen peroxide ($H_2O_2$), which is catalysed by the SOD enzyme, makes this enzyme into an important antioxidant defence in nearly all cells that are exposed to oxygen. SOD thus protects cells against the harmful effects of the $O_2^-$ radical. Three forms of SOD are present in humans. SOD1 is found in the cytoplasm, in nuclear compartments and in the intermembrane space of mitochondria. SOD2 is found in mitochondria and SOD3 in extracellular fluid. The first is a dimer (made up of two subunits), whereas the other two are tetramers (four subunits). SOD1 and SOD3 contain copper and zinc, whereas SOD2 contains manganese in its reactive centre.

The physiological importance of SOD is illustrated by the severe pathologies observed in mice genetically modified to lack this enzyme, and the reversal of these pathologies upon administration of external SOD to the patients.

SOD1 mutations have been linked to amyotrophic lateral sclerosis (ALS), and its inactivation with the development of hepatocellular carcinoma [Elchuri, et al., S. (2005). *CuZn-SOD deficiency leads to persistent and widespread oxidative damage and hepatocarcinogenesis later in life. Oncogene* 24: 367-380]. In addition, mice without SOD1 display an acceleration of age-dependent loss of muscle mass [Muller, et al., F. L. (2006). *Absence of CuZn superoxide dismutase leads to elevated oxidative stress and acceleration of age-dependent skeletal muscle atrophy. Free Radic. Biol. Med* 40: 1993-2004], early incidence of cataracts and a reduced life expectancy.

In mice, the inactivation of SOD2 causes perinatal death, its deficiency killing the new-born mice by massive oxidative stress within a few days of birth [Li, et al., Y. (1995). *Dilated cardiomyopathy and neonatal lethality in mutant mice lacking manganese superoxide dismutase. Nat. Genet.* 11: 376-381].

There are thus numerous diseases linked to the presence of the superoxide anion and the lack or dysfunction of endogenous SOD. These include, for example, inflammatory diseases, such as rheumatoid arthritis, osteoarthritis and Crohn's disease, Parkinson's disease, various types of cancer, Alzheimer's disease, diabetes, fibrosis, psoriasis, asthma, etc. [Maritim A C et al., (2003), *Diabetes. Oxidative stress and antioxidants: a review, J. Biochem. Mol. Toxicol*, 17: 24-38].

SOD is also used in cosmetic products to reduce free radical damage to skin, to reduce fibrosis occurring as a result of radiotherapy, for instance. SOD is known to reduce fibrosis [Vozenin-Brotons, M C. et al. (2001). *Antifibrotic action of Cu/Zn SOD is mediated by TGF-beta1 repression and phenotypic reversion of myofibroblasts. Free Radic Biol Med.* 30 (1): 30-42. PMID 11134893], possibly through the reversion of myofibroblasts to fibroblasts. In addition, SOD is used to treat pain and the effects of chemotherapy and radiation [Lebovitz, et al. (1996) *Neurodegeneration, myocardial injury, and perinatal death in mitochondrial superoxide-deficient mice. Proc. Natl. Acad. Sci. USA.* 93: 9782-9787], [Li et al (1995). *Dilated cardiomyopathy and neonatal lethality in mutant mice lacking manganese superoxide dismutase. Nat. Genet.* 11: 376-381], [Zelko et al (2002) Superoxide dismutase multigene family: a comparison of the CuZn-SOD (SOD1), Mn-SOD (SOD2) and EC-SOD (SOD3) gene structures, evolution and expression. *Free Radic. Biol. Med.* 33:337-349]; [Chen et al. (1998) *Overexpression of MnSOD protects against myocardial ischemia/reperfusion injury in transgenic mice. J. Mol. Cell. Cardiol.* 30:2281-2289], [Keller, et al. (1998) *Mitochondrial manganese superoxide dismutase prevents neural apoptosis and reduces ischemic brain injury suppression of peroxynitrite production, lipid peroxidation, and mitochondrial dysfunction, J. Neurosc.* 18:687-697]; [Flores et al. (1993) *Tat protein of human immunodeficiency virus type 1 represses expression of manganese superoxide dismutase in HeLa cells, Proc. Natl. Acad. Sci. USA,* 90:7632-7636]; [Westendorp et al (1995) *HIV-1 Tat potentiates TNF-induced NF-kappa B activation and cytotoxicity by altering the cellular redox state, Embo. J.,* 14:546-554], [Yan (1999) *Altered levels of primary antioxidant enzymes in progeria skin fibroblasts, Biochem. Biophys. Res. Commun.,* 257:163-167].

The prior art shows that SOD carries out important functions in the body, such as providing protection against cellular oxidative stress and inflammatory or degenerative processes. When SOD activity is disrupted, this causes an increase in oxidative stress, which leads to the development of various disorders or diseases in the human body, including: inflammatory-, carcinogenic- or degenerative processes.

The synthesis of SOD mimetic compounds thus appears necessary to be able to compensate for potential deficiencies in the activity of endogenous SOD or its absence, and thus be able to treat the numerous pathologies or above-mentioned diseases whose common aetiology is the lack of this enzyme or a deficiency in its activity. Ideally, the mimetic compounds synthesised should display reduced toxicity and, in addition, be able to carry out the dismutation reaction with the lowest possible concentration of compound. The use of lower concentrations or doses of SOD mimetics would reduce the cost of treatments, not to mention the risk associated with side effects and the onset of immunogenicity.

No documents have been found in the prior art which specifically disclosed the metal complexes developed in the present invention.

In addition, the metal complexes developed in the present invention address and resolve the technical problems described above, due to the fact that they exhibit reduced toxicity, low $IC_{50}$ index values (see examples of the invention) and do not trigger the development of immunogenicity.

The low $IC_{50}$ value of the metal complexes described in the present invention has important implications, given that the lower the value, the lower the amount of compound required to achieve the desired mimetic effect. The use of a lower quantity of compound to achieve the dismutation reaction will therefore significantly reduce side effects.

In addition, due to their stability in plasma, the metal compounds referred to in the present invention have a long half-life and do not present problems with regard to tissue distribution following administration.

DESCRIPTION OF THE INVENTION

The present invention comprises a process to synthesise SOD-mimetic metal complexes from intermediary compounds which are macrocyclic polyazapyridinophanes with a quinolone heterocycle attached to the central structure of the molecule. The first step of this process thus involves the synthesis of the Formula 1 or 2 intermediary compound, using the synthetic Formula 3 compound as a precursor, the subsequent purification of the intermediary Formula 1 or 2 compound, and lastly, the formation of metal complexes through the binding of purified Formula 1 or 2 compound with metal ions via their nitrogen atoms. FIG. 1 schematically shows how the Formula 1 compound forms a coordination complex with a $Mn^{2+}$ atom.

The intermediary compounds created during the first step of the invention process, using the synthetic Formula 3 compound,

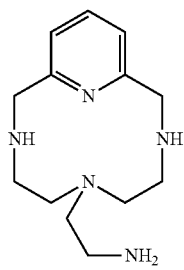

(3)

are characterised by Formula 1, shown below, wherein the quinolone heterocycle is bonded to the 4-position of the methylene which is bonded to the ethylamine chain, or, alternatively, by Formula 2, also shown below, wherein the quinolone heterocycle is bonded to the 2-position of the methylene, which is bonded to the ethylamine chain:

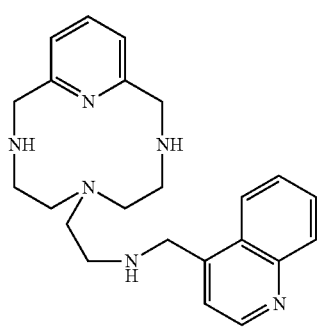

(1)

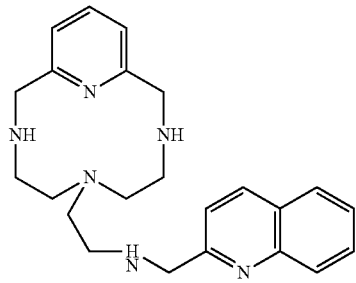

(2)

Intermediary compounds 1 and 2 are isomers, structurally characterised by the fact that they consist of triazapyridinophanes with an ethylamine chain substituted on the tertiary nitrogen of the cycle, which itself comprises a methylquinolil substituent bonded to the amine. Triazapyridinophane is a cyclic compound which includes a pyridine ring and contains three amino(aza) groups in its cyclic chain, as well as an ethylenic chain ending in an amino(aza) group as a substituent of the cycle. The ethylamine chain also contains a methylquinolil group as a substituent of the amino group. As mentioned previously, there are two positions (-2 or -4) at which the quinolone system can be bonded to the methylene which is bonded to the ethylamine chain.

These intermediary compounds belong to a family known as the scorpiands (trisubstituted amine, with three ethylamine chains) of the pyridinophane type (two of the chains form a cycle with the pyridinic ring), the third chain containing different aromatic and/or ethylenaminic substituents bonded to the amino group of the chain.

As mentioned before, once the intermediary Formula 1 or 2 compounds are synthesised, they are isolated and purified by successive washings with ethanol or methanol. The intermediary Formula 1 or 2 compounds are subsequently bonded with metal ions (preferably Cu(II), Fe(II) and Mn(II)) to form SOD-mimetic metal complexes. These complexes can be used therapeutically to treat diseases such as those mentioned in the prior art of the present invention, whose aetiology is based on disturbances in the activity of endogenous SOD or a deficiency in this enzyme. To give an example, the SOD-mimetic complexes referred to in the present invention are used mainly as anti-inflammatories, analgesics and antioxidants protecting against cellular oxidative stress.

It is worth highlighting that in terms of activity, particularly significant results (see Example 3) have been observed with the metal complexes synthesised using the Formula 1 compound and the Mn(II) anion (see FIG. 1).

In the context of the present invention, the term 'metal complex' designates any molecular association between the intermediary Formula 1 or 2 compounds and any metal ion, preferably Cu(II), Fe(II) and Mn(II).

On the other hand, in the context of the present invention, the term 'SOD-mimetic complex' designates a metal complex which is able to mimic, supplement and possibly improve the therapeutic activity and/or functions of endogenous SOD enzyme.

In addition, in the context or the present invention, the term 'effective therapeutic amount' designates one which causes a reversion of the disease treated or leads to an improvement in its symptoms.

The metal complexes described in the present invention can be used as active principles in human patients or animals; they can be prepared into pharmaceutical compositions or formulations, and administered, according to existing knowledge in the prior art of pharmaceutical development, in a number of manners, such as: by intradermal injection, or orally as capsules, caplets or tablets.

Similarly, the solid forms are prepared with the necessary excipients, selected from the group comprising but not limited to: mannitol, polyvinylpirrolidone, microcrystalline cellulose, silica gel, talcum, magnesium stearate, titanium oxide, dyes and antioxidants.

The metal complexes referred to in the invention overcome the problems cited in the prior art thanks to their reduced toxicity and low $IC_{50}$ values. The low $IC_{50}$ value of the metal complexes described in the present invention has significant implications, given that the lower this value, the smaller the amount of complex required to achieve the desired mimetic effect. The use of a lower quantity of compound to achieve the dismutation reaction will therefore significantly reduce side effects.

Furthermore, the metal complexes described in the invention exhibit high stability (Example 2, Table 2) and a long half-life, thus preventing problems associated with tissue distribution after administration and the development of immunogenicity.

The methodology used to study the catalytic decomposition capacity of the superoxide anion in these metal compounds in relation to the native enzyme has been previously described by McCord and Fridovich [C. Beauchamp, I. Fridovich, *Analytical Biochemistry*, 1971, 44, 276] and optimised for Cu(II), Fe(II) and Mn(II) metal complexes.

The first aspect of the present invention thus refers to a process to synthesise SOD-mimetic metal complexes which comprises the coordination of the metal by the nitrogen of the Formula 1 or 2 compounds.

In a favoured implementation of the invention, the process is characterised by the fact that the metal ions bonded to the Formula 1 or 2 compound are selected from the following: Cu (II), Fe (II) and Mn (II).

In another favoured implementation of the invention, this process is characterised by the intermediary Formula 1 and 2 compounds being previously synthesised by means of a process which involves reacting the Formula 3 compound with the 2- or 4-quinoline aldehyde dissolved in ethanol, depending on, respectively; whether the intermediary compound to be synthesised is the Formula 2 or the Formula 1 compound, and the subsequent addition of sodium borohydride to reduce the imine thus formed.

Further aspects of the present invention refer to the actual intermediary Formula 1 or 2 compounds, to their use in the synthesis of SOD-mimetic metal complexes, preferably with Cu (II), Fe (II) or Mn (II) ions, to the metal complex comprising the Formula 1 or 2 compound itself and at last one metal ion, with a preference for Cu (II), Fe (II) or Mn (II), and the use of those metal complexes as SOD enzyme mimetics to produce a pharmaceutical composition intended for the treatment of diseases whose aetiology is rooted in alterations in endogenous SOD activity or, specifically, as an anti-inflammatory, analgesic or agent providing protection against cellular oxidative stress.

EXAMPLES

Example 1

Figure 1:
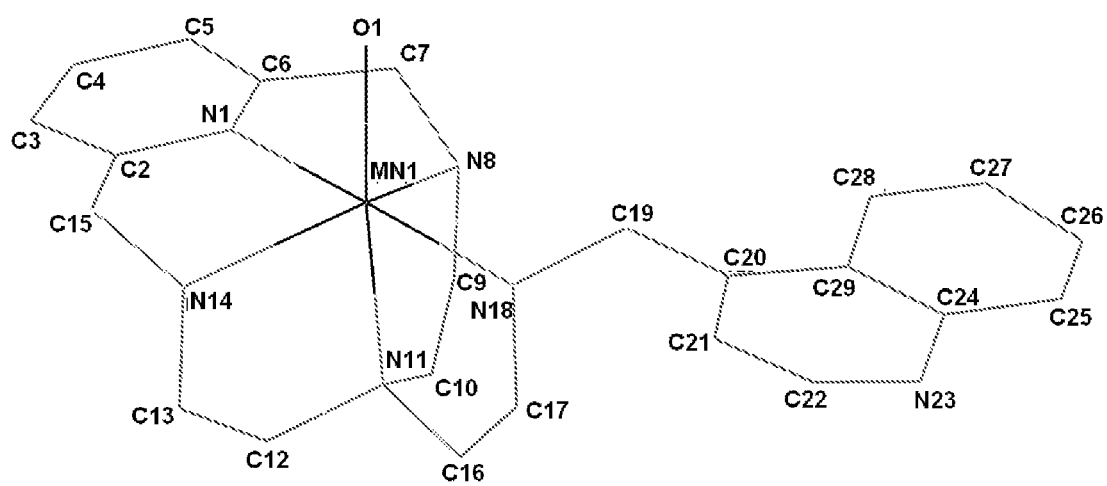
FIG. 1. Diagram of the manner in which the Formula 1 compound forms a coordination complex with a $Mn^{2+}$ atom.
Figure 2:
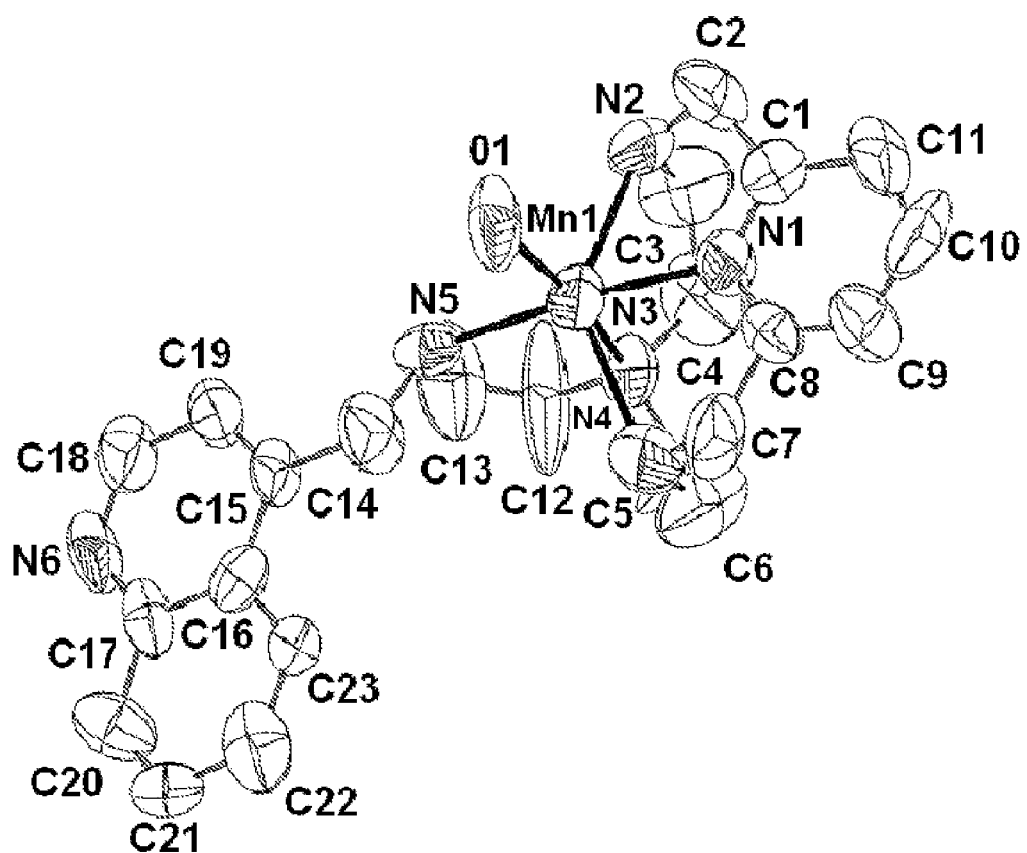
FIG. 2. Crystallographic structure of the metal complex formed using the Formula 1 intermediary compound.
Figure 3:
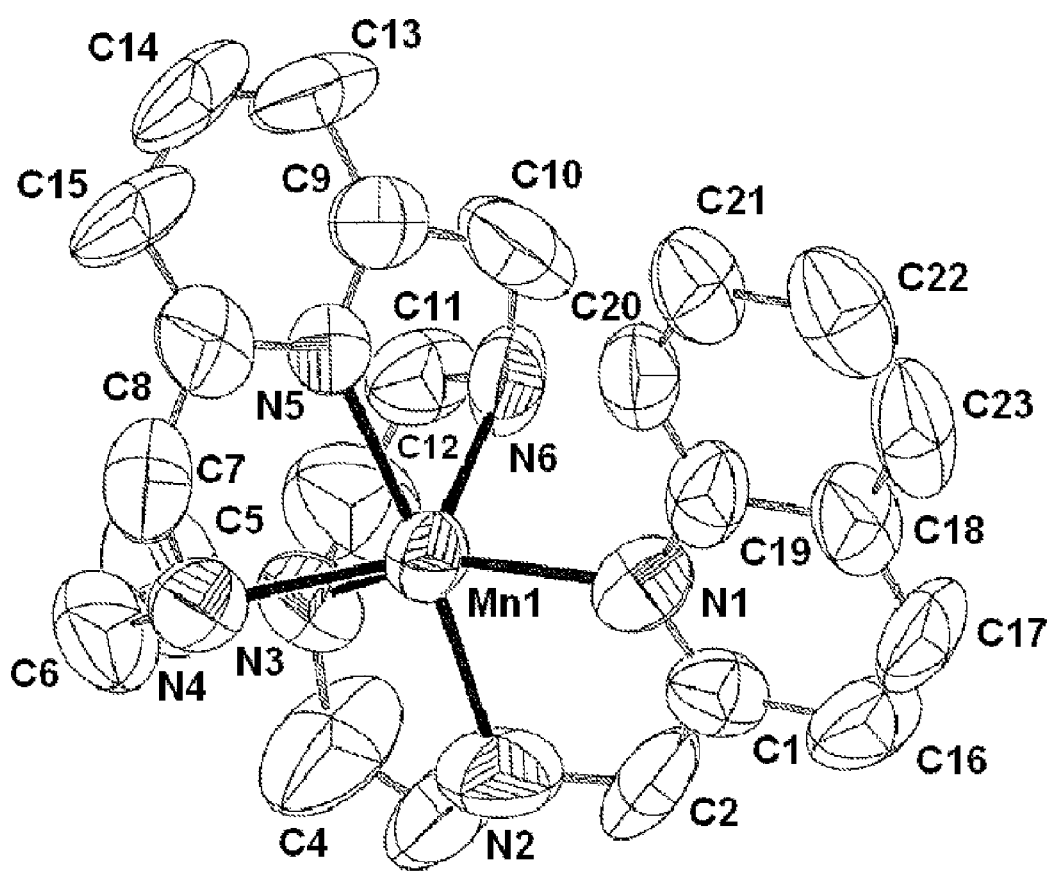
FIG. 3. Crystallographic structure of the metal complex formed using the Formula 2 intermediary compound.

Preparation of Formula 1 and 2 Intermediary Compounds

The synthesis of the intermediary Formula 1 and 2 compounds was carried out by reacting the Formula 3 compound (see diagram I) with the 2-quinoline aldehyde (in the case where the intermediary complex to be synthesised is the Formula 2 compound) or the 4-quinoline aldehyde (in the case where the intermediary complex to be synthesised is the Formula 1 compound), both dissolved in ethanol. Sodium borohydride was subsequently added to reduce the imine thus formed. The mixture undergoes the appropriate treatment to extract the Formula 1 or 2 compound reaction product, which is then used to prepare the ammonium salt by adding hydrochloric acid.

The diagram below shows the process by means of which the Formula 1 or 2 intermediary products are synthesised:

Diagram I

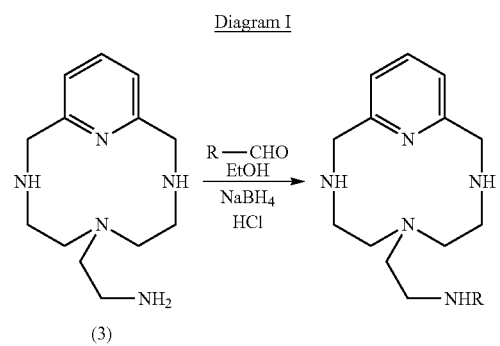

The salts of compounds 1 and 2 are solid and were purified by means of successive washings with ethanol or methanol.

Example 2

Characterisation of Formula 1 and 2 Intermediary Compounds

The Formula 1 and 2 intermediary compounds were fully characterised by NMT spectroscopy, mass spectrometry, crystallographic analysis and elemental analysis.

Potentiometric measurements were performed to determine the acid-base behaviour of the new family of compounds, yielding the overall protonation constants required for the subsequent study on the formation of metal complexes with Cu(II), Fe(II) and Mn(II).

Table 1 shows the logarithms of the protonation constants determined for $NaClO_4$ 0.15 $mol \cdot dm^{-3}$ at 298.1±0.1 K. The charges are omitted. The numbers in brackets indicate the standard deviation of the last significant figure. [a)] The overall basicity constant is $\beta = \Sigma K_{HjL}$

TABLE 1

| Reaction | Comp. 2 | Comp. 1 |
|---|---|---|
| L + H ⇌ HL | 10.03(1) | 9.93(1) |
| HL + H ⇌ H$_2$L | 8.40(1) | 8.31(1) |
| H$_2$L + H ⇌ H$_3$L | 6.23(1) | 5.94(1) |
| H$_3$L + H ⇌ H$_4$L |  | 2.82(1) |
| Log β$^a$ | 24.66(2) | 27.00(1) |

Table 2 shows stability constants for the formation of metal complexes with Mn$^{2+}$, determined in NaClO$_4$ 0.15 mol·dm$^{-3}$ at 298.1±0.1 K. The charges are omitted, and the numbers in brackets indicate the standard deviation of the last significant figure. This table shows the stability constants for the formation of metal complexes with Mn(II). The stability exhibited by complexes formed with the Formula 1 and 2 compounds, which is reflected by the formation constants of their complexes ([Mn(II)-Formula 1 compound]$^{2+}$ (log K=8.91(1) and [Mn(II)-Formula 2 compound]$^{2+}$ (log K=11.08(1)), is sufficient to prevent the dissociation of the complexes in plasma at near-neutral pH. Moreover, the solid compounds [Mn(II)-Formula 1 compound-H$_2$O)](ClO$_4$)$_2$ and [Mn(II)-Formula 2 compound](ClO$_4$)$_2$ were obtained by the slow evaporation, for several weeks, of aqueous solutions of Mn(II) perchlorate and the hydrochloride of the Formula 1 and 2 compounds at neutral pH, taking no precautions regarding the deoxygenation of the solvent. The evaporation was in fact carried out in flasks, in contact with atmospheric oxygen. These experimental observations reveal high stability against atmospheric oxidation and support the aforementioned plasma stability of the compounds which constitute the object of this invention.

TABLE 2

| Reaction | Compound 2 | Compound 1 |
|---|---|---|
| Mn + L ⇌ + MnL | 11.08(1) | 8.91(1) |
| Mn + L + H ⇌ HMnL | 16.23(6) |  |
| Mn + L + H$_2$O ⇌ MnL(OH) + H$^+$ |  | -1.36(1) |
| MnL + H ⇌ HMnL | 5.15(2) |  |
| MnL + OH ⇌ MnL(OH) |  | 3.45(1) |

Table 3 shows the crystallographic data obtained for the metal complexes formed with the Formula 1 and 2 compounds:

TABLE 3

| | Compound 1 | Compound 2 |
|---|---|---|
| Formula |  | C$_{23}$H$_{30}$MnN$_6$Cl$_2$O$_8$ |
| Molecular weight | 662.39 | 644.37 |
| Crystal size, mm | 0.5 0.3 × 0.3 | 0.4 0.2 × 0.2 |
| Crystal system | monoclinic | monoclinic |
| Spatial group | P 21 | P 21 c |
| TK | 293(2) | 293(2) |
| a, Å | 8.938(3) | 15.299(1) |
| b, Å | 15.366(5) | 12.8930(13) |
| c, Å | 10.3010(17) | 28.233(3) |
| α, deg | 90 | 90 |
| β, deg | 94.673(14) | 92.971(7) |
| γ, deg | 90 | 90 |
| V, Å$^3$ | 1410.1(7) | 5561.5(9) |
| Z | 9 | 8 |
| d$_{calc}$ g/cm3 | 1.560 | 1.539 |
| μ, mm$^{-1}$ (MoKα) | 0.719 | 0.725 |
| F(000) | 686 | 2664 |
| Refls. collected | 1913 | 12195 |
| Unique reflections | 1913 | 5066 |

TABLE 3-continued

| | Compound 1 | Compound 2 |
|---|---|---|
| Limitations | 16 | 26 |
| Params. | 370 | 700 |
| Rl. wR2 (all) | 0.0800, 0.2182 | 0.1542, 0.4082 |

Example 3

Figure 4:
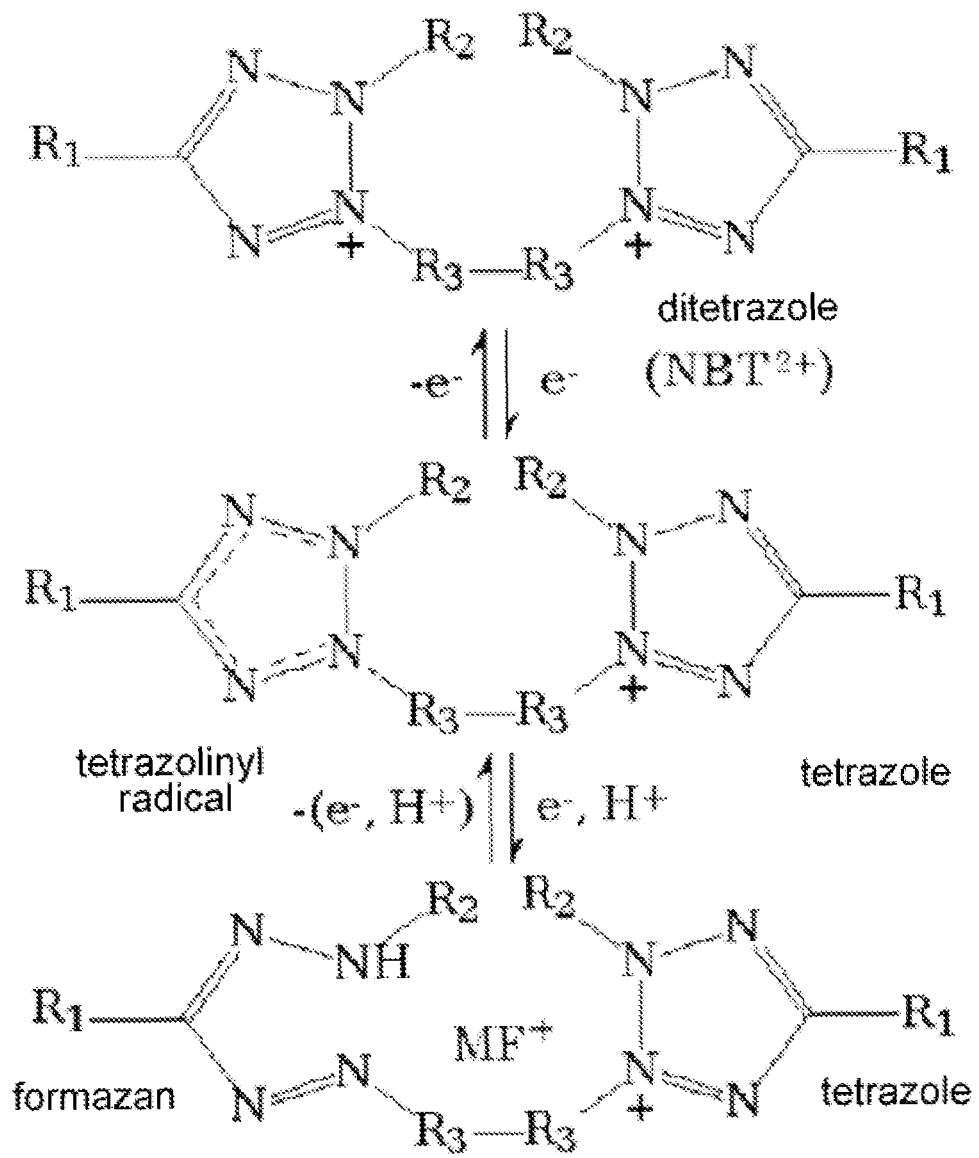
FIG. 4. Diagram depicting the method used to reduce NBT (nitro blue tetrazolium).
Figure 5:
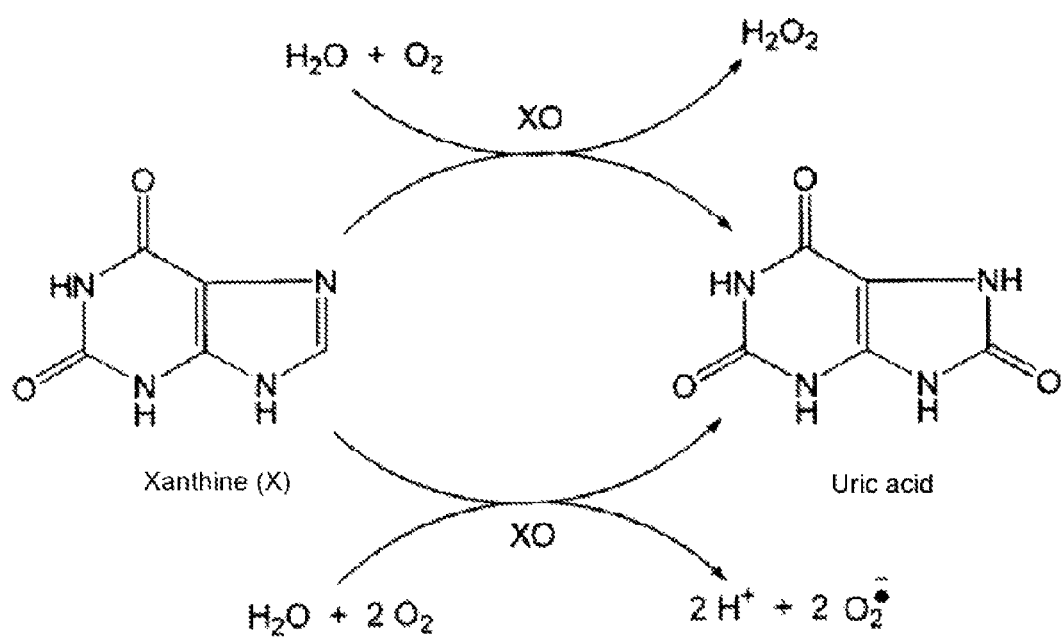
FIG. 5. Formation of superoxide anions from xanthine/xanthine oxidase.

Study of the Activity of the Metal Complexes of the Invention as SOD Enzyme-mimetics The SOD-mimetic activity of these metallic complexes was determined using the method described by McCord and Fridovich which involves the reduction of nitro-blue tetrazolium (NBT) with the superoxide anion (FIG. 4). The superoxide anions were generated using the xanthine oxidase enzyme complex (FIG. 5). These anions are subsequently reacted with the NBT and the compound whose activity needs to be tested.

The assays were performed using a 50 mM HEPES buffer solution at pH 7.4 and a temperature of 25° C. We measured the variation of absorbance at 560 nanometres, using a UV-visible spectrophotometer. Reaction rate values were determined via the variation of absorbance over time, and the IC$_{50}$ and catalytic constant (kcat) obtained, the IC$_{50}$ being determined by means of the following equation:

$$IC_{50} = 1/(1-2f)K$$

and kcat is:

$$kcat = K_{NBT}[NBT]/IC_{50}$$

Table 4 shows the IC$_{50}$ and kcat values obtained for the metal complexes formed with the Formula 1 and 2 compounds and the Mn(II) ion.

TABLE 4

| | Complex 2 | Complex 1 |
|---|---|---|
| IC$_{50}$ (mol L$^{-1}$) | 1.17 × 10$^{-6}$ | 2.39 × 10$^{-7}$ |
| kcat(mol L$^1$ Ls$^{-1}$) | 3 × 10$^7$ | 1.6 × 10$^7$ |

All metal complexes formed using the Formula 1 or 2 compound exhibit significant SOD activity (Kcat), this being especially true of the metal complex formed by using compound 1.

Example 4

Study of the Toxicity of the Metal Complexes of the Invention

Cultures of *Saccharomyces cerevisiae* (*Candida albicans* and mutant strains 96687 and 96688 from the American Type Culture Collection) were grown in liquid YNB medium, in the presence of different concentrations of the SOD-mimetic complexes of the invention (up to 0.5 mM), observation of the cultures indicating normal growth.

It can therefore be concluded that the compounds tested do not exhibit toxicity or inhibit growth.

The invention claimed is:

1. Intermediate compound of Formula 1:

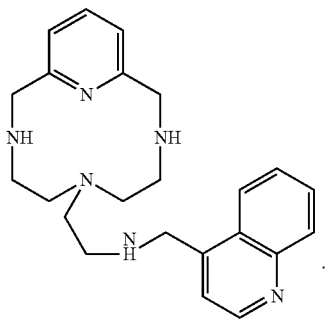

(1)

2. Intermediate compound of Formula 2:

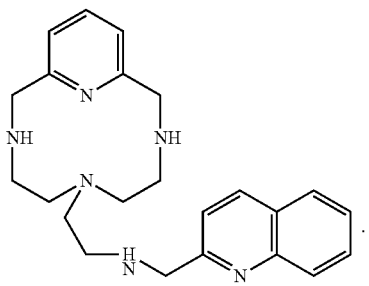

(2)

3. Process for the synthesis of SOD enzyme-mimetic metal complexes which comprises the binding of metal ions to a compound of claim 1.

4. Process, according to claim 3, characterized in that the metal ions which bind to the compound of Formula 1 are selected from: Cu (II), Fe (II) and Mn (II).

5. Process, according to claim 3, characterized in that the intermediate compound of Formula 1 is previously synthesised by means of a process which comprises reacting the compound of Formula 3:

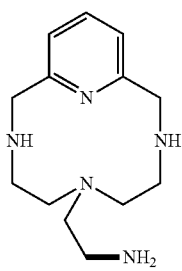

(3)

with 4-quinoline aldehyde dissolved in ethanol and the subsequent addition of sodium borohydride to reduce the imine thus formed.

6. Metal complex which comprises the compound according to claim 1 and at least one metal ion.

7. Metal complex, according to claim 6, wherein the metal ion is selected from: Cu (II), Fe (II) or Mn (II).

8. Metal complex, according to claim 7, wherein the metal ion is Mn (II).

9. Metal complex which comprises the compound according to claim 2 and at least one metal ion.

10. Metal complex, according to claim 9, wherein the metal ion is selected from: Cu (II), Fe (II) or Mn (II).

11. Metal complex, according to claim 10, wherein the metal ion is Mn (II).

12. Pharmaceutical compositions comprising at least one metal complex according to claim 6, or combinations thereof, as their active principle and, optionally, at least one pharmaceutically acceptable excipient.

13. Method for treating diseases whose etiology is based on alterations in the activity of, or a deficiency in endogenous SOD, comprising the administration, to an individual suffering from this disease, of a medicament comprising a therapeutically effective quantity of at least one metal complex according to claim 6, or a combination thereof.

14. The method according to claim 13, wherein the medicament further comprises at least one pharmaceutically acceptable excipient.

15. The method of claim 13, wherein the medicament is used as: an anti-inflammatory, analgesic or compound providing protection against cellular oxidative stress.

16. Process for the synthesis of SOD enzyme-mimetic metal complexes which comprises the binding of metal ions to a compound of claim 2.

17. Process, according to claim 16, characterized in that the metal ions which bind to the compound of Formula 2 are selected from: Cu (II), Fe (II) and Mn (II).

18. Process, according to claim 16, characterized in that the intermediate compound of Formula 2 is previously synthesised by means of a process which comprises reacting the compound of Formula 3:

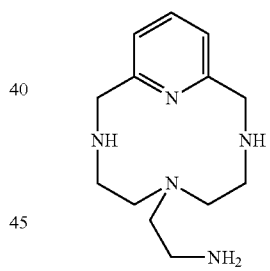

(3)

with 2-quinoline aldehyde dissolved in ethanol and the subsequent addition of sodium borohydride to reduce the imine thus formed.

19. Pharmaceutical compositions comprising at least one metal complex according to claim 9, or combinations thereof, as their active principle and, optionally, at least one pharmaceutically acceptable excipient.

20. Method for treating diseases whose etiology is based on alterations in the activity of, or a deficiency in endogenous SOD, comprising the administration, to an individual suffering from this disease, of a medicament comprising a therapeutically effective quantity of at least one metal complex according to claim 9, or a combination thereof.

21. The method according to claim 20, wherein the medicament further comprises at least one pharmaceutically acceptable excipient.

* * * * *